(12) United States Patent
King et al.

(10) Patent No.: US 9,428,343 B2
(45) Date of Patent: Aug. 30, 2016

(54) APPARATUSES FOR TRANSFERRING ARTICLES AND METHODS OF MAKING THE SAME

(71) Applicant: The Procter & Gamble Company, Cincinnati, OH (US)

(72) Inventors: Scott Alan King, Liberty Township, OH (US); Jennifer Lynn Tuertscher, Cincinnati, OH (US); David Stuart Howell, II, Washington Township, OH (US); Roger George Hasler, Lawrenceburg, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/588,478

(22) Filed: Jan. 2, 2015

(65) Prior Publication Data

US 2016/0194160 A1    Jul. 7, 2016

(51) Int. Cl.
*B65H 39/14* (2006.01)
*B65G 47/24* (2006.01)
*B65G 43/10* (2006.01)
*B65G 47/53* (2006.01)
*B65G 15/24* (2006.01)
*B65G 15/58* (2006.01)
(Continued)

(52) U.S. Cl.
CPC ......... *B65G 43/10* (2013.01); *A61F 13/15764* (2013.01); *B65G 15/24* (2013.01); *B65G 15/58* (2013.01); *B65G 47/244* (2013.01); *B65G 47/53* (2013.01); *B65H 39/14* (2013.01)

(58) Field of Classification Search
CPC . B65H 39/14; A61F 13/15764; B65G 43/10; B65G 47/244
See application file for complete search history.

(56) References Cited

U.S. PATENT DOCUMENTS 4,333,790 A    6/1982    Schaffron
4,429,781 A    2/1984    Holzhauser
(Continued)

FOREIGN PATENT DOCUMENTS

CH    678616    10/1991
EP    0812789    12/1997
(Continued)

OTHER PUBLICATIONS

International Search Report and Written Opinion, PCT/US2015/067982, date of mailing Apr. 1, 2016.
(Continued)

*Primary Examiner* — Thomas Randazzo

(57) ABSTRACT

An apparatus for transferring an article from a first carrier moving at a first speed to a second carrier moving at a second speed is provided. The apparatus comprises a programmable motor and a carrier member operably engaged with the programmable motor. The carrier member comprises a housing comprising a wall defining an interior space and an outer surface configured to receive the article from the first carrier in a receiving zone and configured to deposit the article onto the second carrier in an application zone. The carrier member comprises a support member comprising carbon fiber at least partially positioned within the interior space of the housing and connected with a portion of the wall. The programmable motor is configured to move the outer surface of the carrier member at a third speed through the receiving zone and at a fourth speed through the application zone.

22 Claims, 11 Drawing Sheets

(51) Int. Cl.
  *A61F 13/15* (2006.01)
  *B65G 47/244* (2006.01)

(56) References Cited

U.S. PATENT DOCUMENTS

| | | | |
|---|---|---|---|
| 4,726,876 A * | 2/1988 | Tomsovic, Jr. | A61F 13/15601 156/552 |
| 5,091,039 A * | 2/1992 | Ujimoto | A61F 13/15609 156/164 |
| 5,235,515 A | 8/1993 | Ungpiyakul et al. | |
| 5,556,504 A | 9/1996 | Rajala et al. | |
| 5,684,344 A | 11/1997 | Takei | |
| 5,693,165 A | 12/1997 | Schmitz | |
| 5,693,195 A | 12/1997 | Saito et al. | |
| 5,766,406 A | 6/1998 | Bohn et al. | |
| 5,776,289 A | 7/1998 | Steidinger | |
| 5,888,343 A | 3/1999 | Olson | |
| 5,895,555 A | 4/1999 | Van Den Bergh | |
| 5,965,963 A | 10/1999 | Chitayat | |
| 5,994,798 A | 11/1999 | Chitayat | |
| 6,022,443 A * | 2/2000 | Rajala | A61F 13/15764 156/302 |
| 6,086,694 A * | 7/2000 | Winter | G09F 5/04 118/669 |
| 6,149,755 A | 11/2000 | McNichols et al. | |
| 6,165,306 A | 12/2000 | Rajala | |
| 6,450,321 B1 * | 9/2002 | Blumenthal | A61F 13/15764 156/520 |
| 6,705,453 B2 | 3/2004 | Blumenthal et al. | |
| 6,814,217 B2 * | 11/2004 | Blumenthal | A61F 13/15764 156/520 |
| 6,942,086 B2 * | 9/2005 | Bridges | B65H 5/12 198/377.08 |
| 7,811,403 B2 * | 10/2010 | Andrews | A61F 13/15756 156/238 |
| 8,100,253 B2 * | 1/2012 | Walsh | A61F 13/15764 198/377.08 |
| 9,227,794 B2 * | 1/2016 | Papsdorf | A61F 13/15764 |
| 2003/0079330 A1 * | 5/2003 | Stopher | B65H 39/14 29/430 |
| 2003/0121614 A1 | 7/2003 | Tabor et al. | |
| 2005/0145322 A1 | 7/2005 | Hoffman et al. | |
| 2013/0270065 A1 * | 10/2013 | Papsdorf | A61F 13/15764 198/377.01 |
| 2013/0270066 A1 | 10/2013 | Papsdorf et al. | |
| 2013/0305511 A1 * | 11/2013 | Schoultz | A61F 13/15756 29/428 |
| 2014/0110052 A1 | 4/2014 | Findley et al. | |
| 2014/0110226 A1 | 4/2014 | Findley et al. | |
| 2014/0174883 A1 | 6/2014 | Papsdorf et al. | |

FOREIGN PATENT DOCUMENTS

| | | |
|---|---|---|
| JP | 2001025285 | 1/2001 |
| WO | WO-9519752 | 7/1995 |

OTHER PUBLICATIONS

All Office Actions, U.S. Appl. No. 14/588,464.
All Office Actions, U.S. Appl. No. 14/588,469.

* cited by examiner

APPARATUSES FOR TRANSFERRING ARTICLES AND METHODS OF MAKING THE SAME

FIELD

The present disclosure is generally directed to apparatuses for transferring articles and methods for making the same and, is more particularly directed to apparatuses for transferring articles from a first carrier moving at a first speed to a second carrier moving at a second speed and methods for making the same.

BACKGROUND

Disposable absorbent articles, such as disposable diapers, generally have been manufactured by a process where articles, discrete articles, or components of different materials, such as leg elastics, waist elastics, ears, tapes, fasteners, or other components have been applied to a substrate (e.g., a chassis of a diaper or a web of chassis material) supported on a continuously moving carrier. Often, the speed at which the articles are fed into the process on a carrier is not the same as the speed of the continuously moving carrier conveying the substrate. Thus, the speed of the articles must be changed, using a transfer apparatus, to match the speed of the continuously moving carrier to properly apply the articles to the substrate without adversely affecting the process or the finished product.

Similarly, labels or stickers are typically placed onto a moving substrate when the speed at which the labels or stickers are fed into the process is not the same as the speed of the moving substrate to be labeled or stickered. Thus, the speed of the labels or stickers must be changed, using a transfer apparatus, to match the speed of the moving substrate to properly apply the labels or stickers to the substrate without adversely affecting the process or the finished product.

Transfer apparatuses for the articles may generally comprise a motor and a carrier member operably engaged with the motor. Previously carrier members were typically formed of a housing and one or more support members, all formed of extruded aluminum as a single piece. The housing comprises an outer surface configured to receive one or more of the articles to be transferred. The housing is rotated by the motor such that the outer surface receives the article from a first moving carrier in a receiving zone and deposits the article onto a substrate being conveyed by a second moving carrier in an application zone. Considering that the speed of the first and second moving carriers is typically different, the carrier member is typically rotated at a variable rate of speed to account for the different speeds of the first and second moving carriers. Typically, the motors of the transfer apparatuses are operably linked to a motor control system, which may comprise an amplifier and/or a controller, to causes the motor to vary the speed of rotation of the housing.

Since previous carrier members, including the one or more support members, were formed of a single extruded aluminum piece, the overall geometries of the carrier members were somewhat limited because of the strength and the required structural configuration of the aluminum support members. What is needed are carrier members having support members formed at least partially of materials other than extruded aluminum that provide a greater degree of flexibility in the design of the overall geometries of the carrier members, a lighter weight, and a higher strength.

SUMMARY

To resolve the above described problem in regard to the limited design of the overall geometries of carrier members formed of extruded aluminum, the present disclosure provides carrier members that comprise a lighter weight and higher strength extruded aluminum housing comprising a wall defining an interior space and a support member. The support member is at least partially formed of carbon fiber and is positioned within the interior space and at least partially connected to the wall using, for example, an adhesive. The support member may provide structural support to the housing of the carrier member and allow for more flexibility in the design of the overall geometries of the carrier member compared to an extruded aluminum support member. Furthermore, the strength of the support members comprising carbon fiber may allow for less aluminum to be used in a housing of a carrier member, thereby providing a lighter carrier member. The support member may comprise carbon fiber, layers of carbon fiber, and/or carbon fiber composites (herein together referred to as "carbon fiber").

In a form, the present disclosure is directed, in part, to an apparatus for transferring one or more articles from a first carrier moving at a first speed to a second carrier moving at a second speed that is different than the first speed. The apparatus comprises a programmable motor and a carrier member operably engaged with the programmable motor. The carrier member comprises a housing comprising a wall defining an interior space and an outer surface configured to receive the one or more articles from the first carrier in a receiving zone and configured to deposit the one or more articles onto the second carrier in an application zone. The carrier member comprises a support member comprising carbon fiber at least partially positioned within the interior space of the housing and connected with a portion of the wall. The programmable motor is configured to move the outer surface of the carrier member at a third speed through the receiving zone and at a fourth speed through the application zone.

In a form, the present disclosure is directed, in part, to an apparatus for transferring one or more articles from a first carrier to a second carrier. The apparatus comprises a first programmable motor, a second programmable motor, a first carrier member operably engaged with the first programmable motor, and a second carrier member operably engaged with the second programmable motor. The first programmable motor is configured to rotate the first carrier member in an orbital path and the second programmable motor is configured to rotate the second carrier member in the orbital path. The first carrier member comprises a housing comprising a wall defining an interior space and an outer surface configured to receive the one or more articles from the first carrier in a receiving zone and configured to deposit the one or more articles onto the second carrier in an application zone. The first carrier member further comprises a support member comprising carbon fiber at least partially positioned within the interior space of the housing and attached to a portion of the wall. The second carrier member comprises a housing comprising a wall defining an interior space and an outer surface configured to receive the one or more articles from the first carrier in the receiving zone and configured to deposit the one or more articles onto the second carrier in the application zone. The second carrier member further comprises a support member comprising carbon fiber at least partially positioned within the interior space of the housing and attached to a portion of the wall. The first and second carrier members are located at least partially between the first and second programmable motors.

In a form, the present disclosure is directed, in part, to an apparatus for transferring one or more articles from a first carrier to a second carrier. The apparatus comprises a first programmable motor, a second programmable motor, a first transfer member operably engaged with the first programmable motor, and a second transfer member operably engaged with the second programmable motor. The first and second transfer members are generally aligned with respect to a common axis. The apparatus comprises a first carrier member connected with the first transfer member. The first transfer member is configured to guide the first carrier member in an orbital path. The first carrier member comprises a housing comprising a wall defining an interior space and an outer surface configured to receive the one or more articles from the first carrier in a receiving zone and configured to deposit the one or more articles onto the second carrier in an application zone. The first carrier member further comprises a support member comprising carbon fiber positioned at least partially within the interior space of the housing and connected with a portion of the wall. The apparatus comprises a second carrier member connected with the second transfer member. The second transfer member is configured to guide the second carrier member in the orbital path. The second carrier member comprises a housing comprising a-wall defining an interior space and an outer surface configured to receive the one or more articles from the first carrier in the receiving zone and configured to deposit the one or more articles onto the second carrier in the application zone. The second carrier member further comprises a support member comprising carbon fiber at least partially positioned within the interior space of the housing and connected with a portion of the wall.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein.

DETAILED DESCRIPTION

Figure 1:
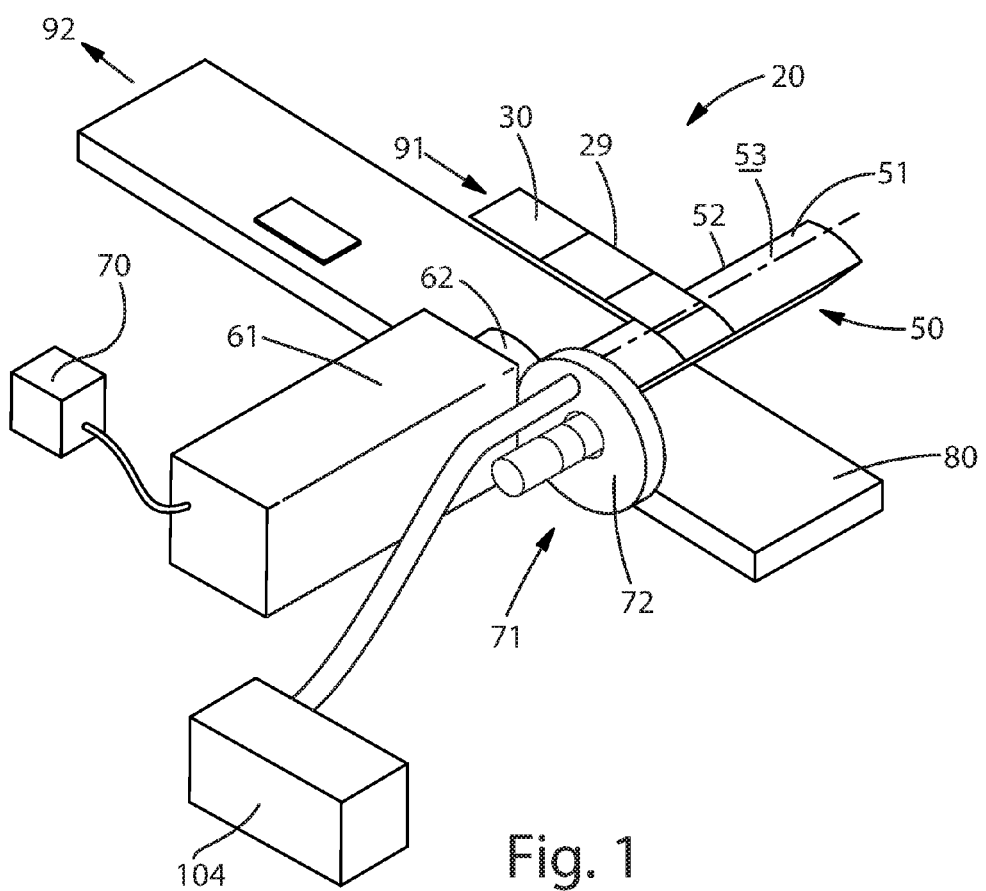
FIG. 1 is a perspective view of an example transfer apparatus used to transfer one or more articles from a first carrier moving at a first speed to a second carrier moving at a second speed in accordance with the present disclosure.

Various non-limiting forms of the present disclosure will now be described to provide an overall understanding of the principles of the structure, function, manufacture, and use of the apparatuses for transferring articles and methods for making the same disclosed herein. One or more examples of these non-limiting forms are illustrated in the accompanying drawings. Those of ordinary skill in the art will understand that the apparatuses for transferring articles and methods for making the same described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

DEFINITIONS

As used herein, the term "absorbent article" refers to disposable devices such as infant, child, or adult incontinence diapers, training pants, incontinence pants, sanitary napkins, and the like which are placed against or in proximity to the body of the wearer to absorb and contain the various exudates discharged from the body (e.g., menses, runny BM, and urine). Typically, these articles comprise a topsheet, backsheet, an absorbent core, optionally an acquisition system (which may be comprised of one or several layers), and typically other components, with the absorbent core normally placed at least partially between the backsheet and the acquisition system or between the topsheet and the backsheet. The absorbent articles may take on any suitable configuration.

As used herein, the term "machine direction" is used herein to refer to the primary direction of material or web flow through a process or manufacturing line.

As used herein, the term "cross machine direction" or "cross machine directional" is used herein to refer to a direction that is generally perpendicular to, or perpendicular to, the machine direction.

The present disclosure provides apparatuses for receiving articles or discrete articles from a first moving carrier traveling at a first speed and applying the articles to a substrate (e.g., absorbent article chassis) on a second moving carrier traveling at a second speed and methods for making the same. The apparatuses are particularly useful for applying any article or component to a substrate useful in the making of disposable absorbent articles and/or for placing labels or stickers onto any suitable articles or substrates.

Those of skill in the art will recognize that the apparatuses of the present disclosure may also be used for applying any suitable article to any suitable substrate, component, web, or other material being conveyed by a moving carrier. As additional non-limiting examples, the articles being transferred by the apparatuses of the present disclosure may be pads, wipes, towels, cellulosic materials, nonwoven materials, tow materials, cleaning substrates, polishing substrates, and/or scrubbing substrates.

Figure 2:
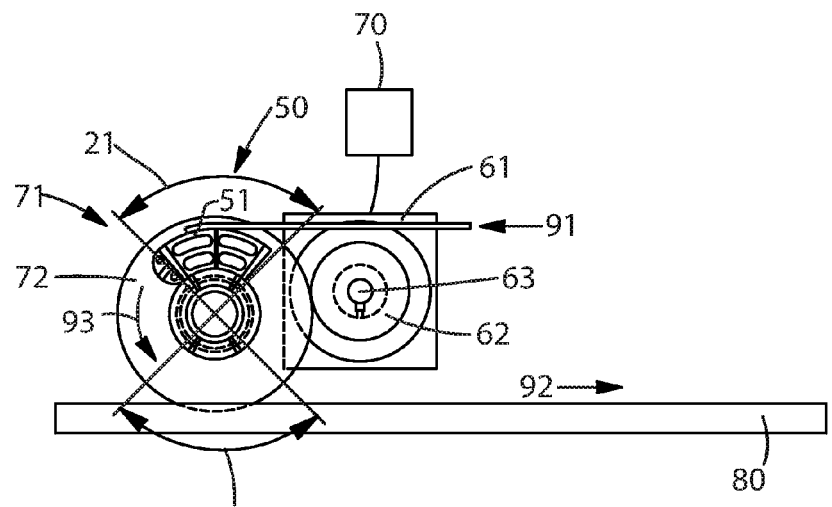
FIG. 2 is a schematic side view of the transfer apparatus of FIG. 1, in accordance with the present disclosure.

Referring to FIGS. 1 and 2, an example transfer apparatus is illustrated. The transfer apparatus 20 may receive discrete articles 30 traveling on a first moving carrier 29 moving at a first speed in the direction indicated by arrow 91 and may apply the articles 30 to a second moving carrier 80 traveling at a second speed in the direction indicated by arrow 92. The transfer apparatus 20 may comprise a motor 61 for transmitting rotational energy to a transfer member 71. The motor 61 may be operably linked or operably engaged with the transfer member 71 using any technique known to those skilled in the art such as, for example, a gear to gear connection, transmission belting and pulleys, gearboxes, direct couplings, and the like or any combinations thereof. For example, in FIG. 1 the transfer member 71 may comprise a driven gear 72 that is connected to a driving gear 62, which transmits rotational energy to the driven gear 72. In use, the driving gear 62 may engage and rotate the driven gear 72 which, in turn, may rotate a carrier member 50 of the transfer apparatus 20.

The illustrated example of the carrier member 50 comprises at least one housing 51 operably connected to the transfer member 71. In some instances, the transfer member 71 may form a portion of the carrier member 50. In such an instance, the transfer member 71 may be positioned more proximal to the motor 61 than the carrier member 50. The housing 51 may comprise a wall 52 and an outer surface 53. The wall 52 may define an interior space 56 (see FIGS. 8 and 9) within the housing 51. A support member 54 (discussed later with respect to FIGS. 8 and 9) may be at least partially positioned within the interior space 56 of the housing 51. The support member 54 may be connected with a portion of the wall 52. The support member 54 may comprise carbon fiber. The wall, or other portions of the housing 51, may also comprise carbon fiber. In one instance, the wall, or other portions of the housing 51 may comprise aluminum or other suitable metal or material. The housing 51 of the carrier member 50 may be connected to the transfer member 71 by any technique known to those skilled in the art such as, for example, bolts, screws, pins, keys and matching key ways, connector parts such as shafting or brackets, adhesive bonding or gluing, welding and the like or combinations thereof. For instance, the housing 51 shown in FIG. 1 may be connected directly to the driven gear 72 by fitting the end of the housing 51 into a mating hole in the driven gear 72 and locking it into position with a pin. Similarly, other components of the transfer apparatus 20 may be connected together employing the above described assembly techniques.

The dimensions of the housing 51 may vary depending upon the desired output of the transfer apparatus 20 and the size and shape of the articles 30 being transferred. The housing 51 may comprise a crescent-shaped member having an outer, peripheral arc length spanning from about 5 degrees to about 355 degrees, an outer radius ranging from about 10 mm to about 1,000 mm or about 25 mm to about 500 mm, and a width ranging from about 25 mm to about 1,000 mm or about 50 mm to about 750 mm, specifically reciting all 0.1 mm increments within the above-specified ranges and all ranges formed therein or thereby. Other suitable dimensions are also within the scope of the present disclosure. As the transfer member 71 rotates, the carrier member 50 may travel in the direction indicated by arrow 93 as shown in FIG. 2. The circumferential, outer peripheral surface of the housing 51 defined by an outer radius may travel along and define an orbital path that passes through a receiving zone 21 and an application zone 23. The receiving zone 21 and the application zone 23 are defined by the respective regions of the orbital path traveled by the housing 51. The receiving zone and the application zone may be otherwise situated as well, as will be recognized by those of skill in the art.

The first moving carrier 29 may be moving at a first speed through the receiving zone 21 and the second moving carrier 80 may be moving at a second speed through the application zone 23. The motor 61 may be configured to move the outer surface 53 of the housing 21 at a third speed through or in the receiving zone 21 and at a fourth speed through or in the application zone 23. The first speed may be equal to, or substantially equal to, the third speed and the second speed may be equal to, or substantially equal to, the fourth speed to effectuate proper controlled transfer of the articles 30.

One illustrated example of the motor 61 comprises a rotatable circular driving gear 62 connected to an input shaft 63. In this example, the input shaft 63 is the output shaft of the motor 61. The transfer member 71 is placed parallel to the motor 61 such that the driving gear 62 meshes with the driven gear 72 using gear set-ups known to those skilled in the art. In use, the motor 61 rotates the input shaft 63 which rotates the driving gear 62 which, in turn, rotates the driven gear 72 and the carrier member 50.

In other forms, the transfer member 71 may comprise any mechanism known to those skilled in the art by which rotational energy may be conducted from one shaft to another such as, for example, v-belts, timing belts, continuous chains and the like or combinations thereof. Further, the transfer member 71 may comprise any mechanism known to those skilled in the art by which input velocity can be variably modified to an output source such as, for example, cams, linkages, and the like or combinations thereof as long as the changes in rotational speed are substantially created by the motor 61.

It will be further appreciated that the transfer apparatuses 20 of the present disclosure may utilize one or, in the alternative, two, or three or more combinations of carrier members 50 (having any number of housings 51, such as two, three, or four), transfer members 71, and motors 61 in series to achieve the desired application of the article to the second moving carrier 80. The different combinations may allow the use of a continuously moving web or substrate to supply the discrete articles. In addition, greater speed ratio differential may be achieved by using combinations of transferring devices, driven mechanisms, driving mechanisms and motors in series.

Figure 3:
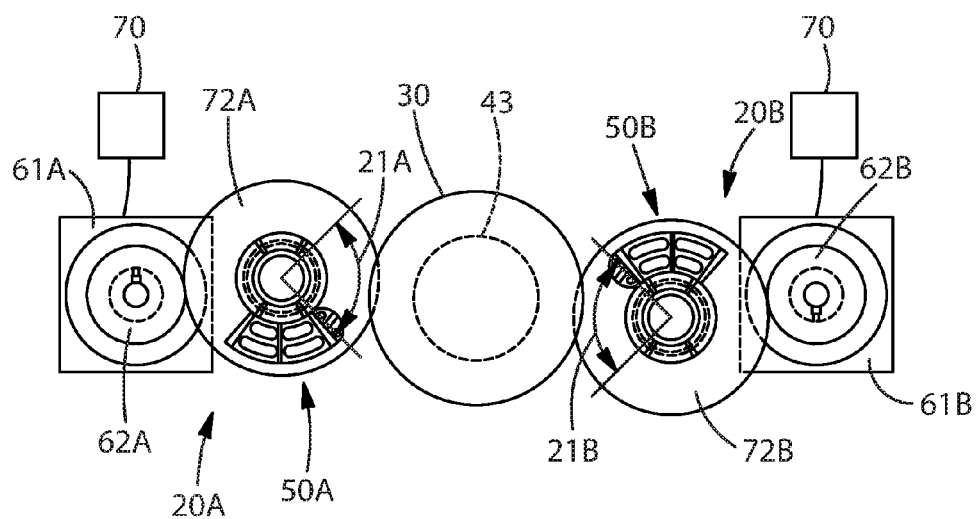
FIG. 3 is a schematic side view of two transfer apparatuses being used together in accordance with the present disclosure.

It will be further appreciated that the transfer apparatus 20 of the present disclosure, when used in series, do not need to operate at the same receiving zone 21 and application zone 23. For example, referring to FIG. 3, there is representatively shown a transfer apparatus 20A comprising a carrier member 50A connected to a motor 61A by a driving gear 62A and driven gear 72A and a second transfer apparatus 20B comprising a carrier member 50B connected to a motor 61B by a driving gear 62B and a driven gear 72B. The transfer apparatus 20A uses a receiving zone 21A to accept articles 30 from a drum 43, while the transfer apparatus 20B uses a receiving zone 21B to accept articles 30 from the same drum 43 at a different rotational position on the drum.

Figure 4:
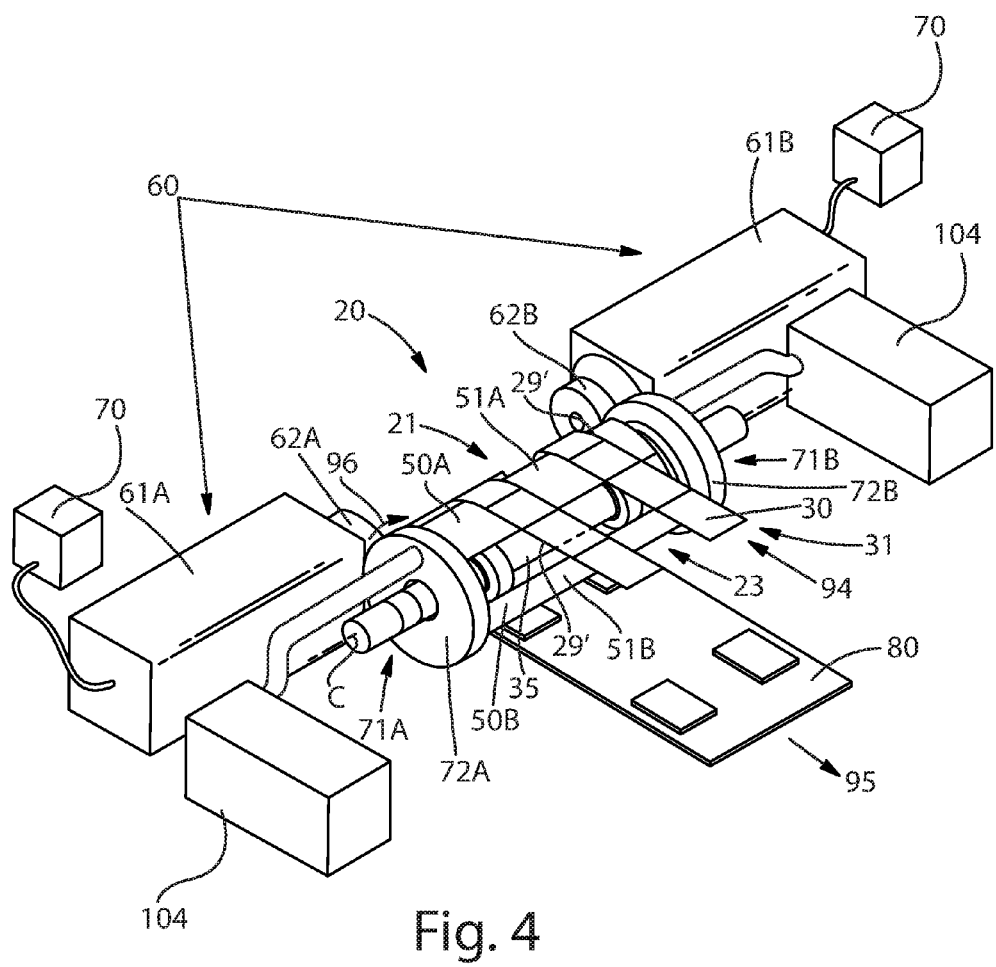
FIG. 4 is a perspective view of an example form comprising two transfer apparatuses used to transfer one or more articles from a first carrier moving at a first speed to a second carrier moving at a second speed in accordance with the present disclosure.

Another aspect of the present disclosure is illustrated, for example, in FIG. 4. A transfer apparatus 20 for receiving discrete articles 30 of a web of a material 31 traveling at a first speed in the direction indicated by arrow 94 is illustrated. The transfer apparatus 20 applies the articles 30 to the second moving carrier 80 traveling at a second speed in the direction indicated by arrow 95. The illustrated example of the transfer apparatus 20 comprises two rotatable carrier members, represented by 50A and 50B, for receiving and applying the articles 30. The transfer apparatus 20 may comprise a driving system 60 having two motors 61A and 61B, each of which may comprise a driving gear 62A, 62B for transmitting rotational energy to the transfer members 71A, 71B represented by the driven gears 72A, 72B.

As illustrated in FIG. 4, each carrier member 50A and 50B may comprise a housing 51A, 51B connected to or formed with the driven gear 72A, 72B. As each of the driven gears 72A, 72B rotate, the carrier members 50A, 50B travel in the direction indicated by arrow 96. In use, the circumferential, outer peripheral surface of the housings 51A, 51B travel along and define an orbital path that passes through the receiving zone 21 and the application zone 23 defined by the respective regions of the orbital path traveled by the housings 51A, 51B of the carrier members 50A and 50B. The first and second transfer members 71A, 71B are generally aligned with respect to a common axis, C. A stationary shaft 35 may rotatable support the first and second transfer members 71A and 71B using bearings or other suitable methods. The stationary shaft 35 may be coaxially oriented along the common axis, C. The stationary shaft 35 may provide support to the transfer members and the carrier members. The first and second carrier members 50A and 50B may be least partially located between the first and second motors 61A, 61B. The first and second transfer members 71A, 71B, may also be at least partially located between the first and second motors 61A, 61B.

The size and shape of the housings 51A and 51B may vary as the number of housings per transfer apparatus changes. For example, if the machine includes two transfer apparatuses as representatively illustrated in FIG. 4, each of the housings 51A and 51B may have an outer peripheral arc length which spans from about 5 to about 175 degrees of the orbital path of the carrier members 50A and 50B.

Each transfer member 71A, 71B may comprise any mechanism known to those skilled in the art by which rotational energy may be conducted from one shaft to another such as, for example, v-belts, timing belts, continuous chains and the like or combinations thereof. Further, the transfer members 71A, 71B may comprise any mechanism known to those skilled in the art by which input velocity can be variably modified to an output source such as, for example, cams, linkages, and the like or combinations thereof as long as the changes in rotational speed are substantially created by the motor 61.

For receiving the articles in the receiving zone 21, the carrier member, as representatively illustrated in the various configurations, may comprise a gripping mechanism so that the outer concave surface of the housing may capture an article in the receiving zone 21 and transport the article to the application zone 23. In such an instance, the gripping mechanism may comprise a fluid pressure (e.g., vacuum) that may be selectively imposed through fluid ports in the housing leading to the outer surface of the housing. For instance, the fluid pressure may be activated in the receiving zone 21 to seize the articles and deactivated in the application zone 23 to release the articles to the second moving carrier 80. In other instances, a negative fluid pressure (i.e., vacuum) may be activated in the receiving zone 21 to seize the articles and a positive fluid pressure may be activated in the application zone 23 to "blow off" the articles onto the second moving carrier 80. In this manner, control may be maintained over the articles at all times during the transfer process between the receiving and application zones. Alternatively, the gripping mechanism may comprise any technique known to those skilled in the art for gripping and releasing articles such as, mechanical clamps, electrical clamps, magnetic clamps and the like or combinations thereof.

For transferring the articles 30 to the second moving carrier 80 in the application zone 23, the transfer apparatus 20 may comprise any of a variety of options known to those skilled in the art such as, adhesive applied on the article, adhesive applied on the moving carrier, an electrostatic charge between the article and moving carrier, vacuum on the moving carrier and the like or combinations thereof. In a form, the transfer may comprise the generation of a weld between the article and the carrier by any of a variety of means known to those skilled in the art such as, pressure generation at a nip formed between the housing and the moving carrier at transfer, interaction between a pattern on the housing and an ultrasonic horn behind the moving carrier at transfer, and the like, or combinations thereof. In addition, in order to aid the welding process, the part may be modified on the housing by energy addition using any mechanism known to those skilled in the art such as, for example, hot air currents, ultraviolet lighting, laser bombardment and the like, or combinations thereof.

The motor may comprise a programmable motor, such as a programmable rotary motor or a programmable linear motor. In other instances, a programmable rotary motor may be used on one transfer apparatus and a programmable linear motor may be used on another transfer apparatus. In still other instances, two programmable rotary motors may be used on two different transfer apparatuses or two programmable linear motors may be used on two different transfer apparatuses. The use of a programmable motor in the transfer apparatus may provide an inexpensive and adaptable method for receiving the articles 30 from the first moving carrier 29 traveling at a first speed and applying the articles 30 to the second moving carrier 80 traveling at a second different speed. The variable angular velocity of the carrier member may be produced by varying the current supplied to the motor. Since the transfer member is operably coupled to the output of the motor, changes in the angular velocity and position of the motor may directly correlate to changes in the angular velocity and position of the carrier member. The current supplied to the motor may be controlled using any of a variety of methods for programming motors known to those skilled in the art such as, standard cam curve functions, a reference data table containing reference points, desired motor encoder points, and the like or combinations thereof.

The programmable motors used to drive the carrier members may provide variable angular velocities including periods where the velocity remains constant for a fixed duration. These constant velocity dwell times may be advantageous in the receiving zone 21 and the application zone 23 particularly when the pick-up and transfer occurs over substantial arc lengths of contact. Alternatively, one or more of the constant speed regions may be changed to a controlled variable speed region. This may enable the article 30 to be picked up in the receiving zone 21 at a variable speed, which, when the part 30 is elastic, would allow tensions to be varied incrementally therein which may be desirous in certain product features. In another example, the constant speed of the motor 61 in the application zone 23 may be such that the corresponding speed of the carrier member is different from speed of the second moving carrier 80 at transfer. Such speed variations generate tension in the article 30 by incrementally transferring the article 30 in a controlled manner from one moving carrier traveling at one surface speed to a second moving carrier traveling at a second surface speed.

It will be further appreciated that the velocity of the carrier member 50 outside of the application zone 23 or the receiving zone 21 may be tailored to aid the performance of secondary processes including adhesive application, printing of identification or registration marks, application of bonding aids, moisture addition and the like and combinations thereof. Such changes in velocity may be beneficial by presenting specific velocity profiles or even additional periods of constant velocity, which may allow for more precise interaction with the secondary processes being performed.

Programmable motors may be purchased from any number of suppliers of programmable motors such as Rockwell Automation, located in Milwaukee, Wis. Further, the program inputs to the motors can be generated by one of ordinary skill in the art if provided with the analytical representation of the desired output function. For instance, the creation of the electronic cam profile for the motor may be developed by first determining the key input variables. The key input variables are based on desired product features, the base design of the transfer apparatus 20 and the desired cycle speed of the transfer apparatus 20. Secondly, the radius of the outer surface of the carrier member 50 is determined. Once the radius is determined, the required cam inputs of rotational velocities, distances traveled and time available for acceleration may be calculated, which serve as the input to the cam profile generator. Additional details regarding these calculations are disclosed, for example, in U.S. Pat. No. 6,450,321 to Blumenthal et al.

Figure 5:
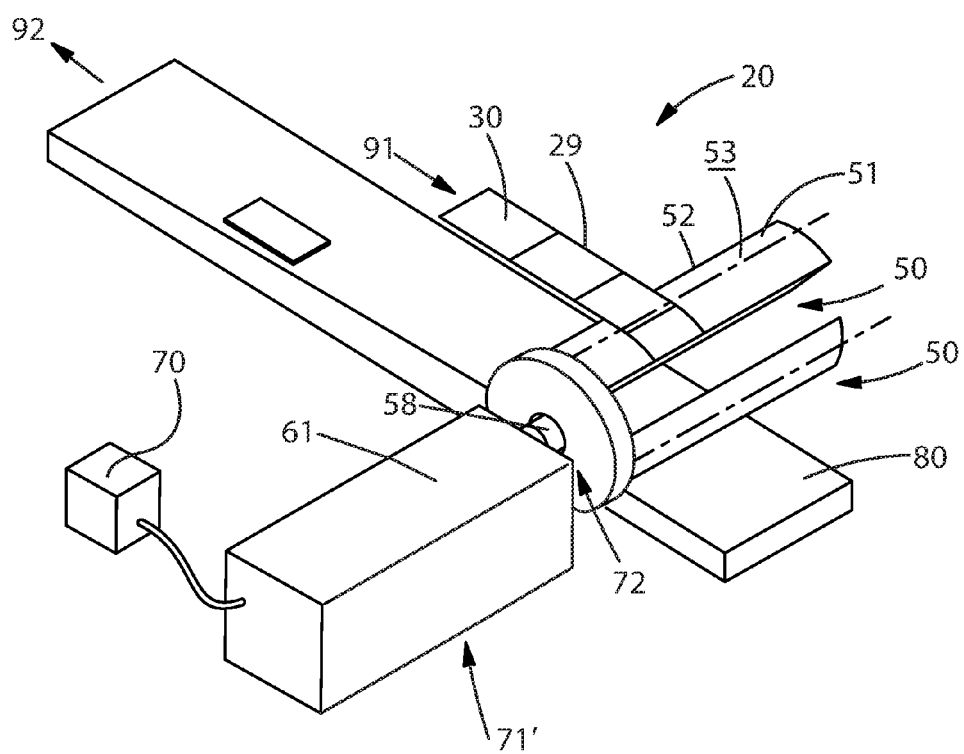
FIG. 5 is a perspective view of an example transfer apparatus used to transfer one or more articles from a first carrier moving at a first speed to a second carrier moving at a second speed in accordance with the present disclosure.
Figure 6:
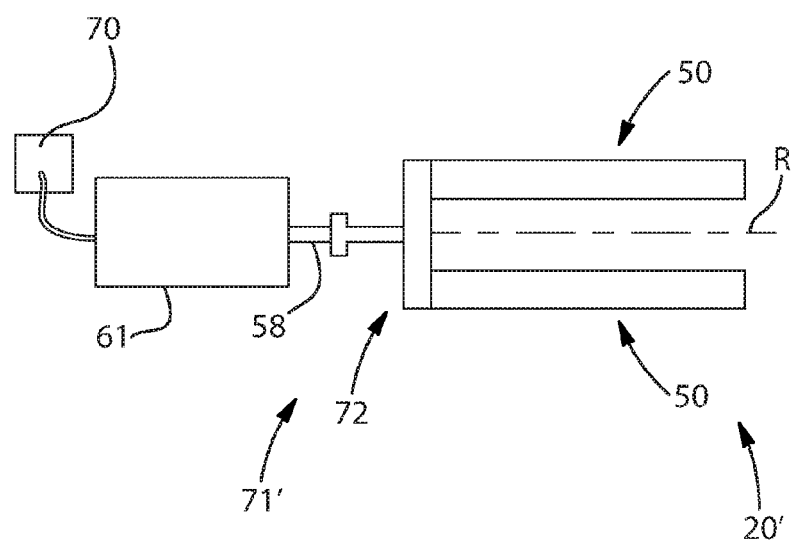
FIG. 6 is a side view of the transfer apparatus of FIG. 5, in accordance with the present disclosure.

Referring to FIGS. 5 and 6, an example form of the transfer apparatus of the present disclosure is illustrated. The transfer apparatus 20' may comprise one or more carrier members 50 engaged with or formed with a transfer member 72, and a motor or programmable motor 61. The transfer member 72 may be directly engaged with a drive shaft 58 of the motor or programmable motor 61. This is known as direct drive. Thus, the transfer member 72 is directly driven by the drive shaft 58 of the programmable motor 61. Stated another way, when the drive shaft 58 is rotated, the transfer member 72 is rotated about an axis of rotation, R. The carrier members 50, owing their engagement with the transfer member 72, are then are orbited about the axis of rotation, R. In some instances, another transfer apparatus (not illustrated), similar to the transfer apparatus 20' may be provided on an opposite side of the second moving carrier 80. In such an instance, a first carrier member may be operably engaged with or directly engaged with a first transfer member which is operably engaged with or directly engaged with a first programmable motor, wherein the first programmable motor is configured to rotate the first carrier member in an orbital path, and wherein the first transfer member is configured to guide the first carrier member in the orbital path. A second carrier member may be operably engaged with or directly engaged with a second transfer member which is operably engaged with or directly engaged with a second programmable motor, wherein the second programmable motor is configured to rotated the first carrier member in the orbital path, and wherein the second transfer member is configured to guide the second carrier member in the orbital path. The first and second carrier members and optionally the first and second transfer members may be at least partially, or fully, located between the first and second programmable motors. In other instances, the transfer members may not be provided and the carrier members may be directly engaged with the drive shafts of the programmable motors.

Figure 7:
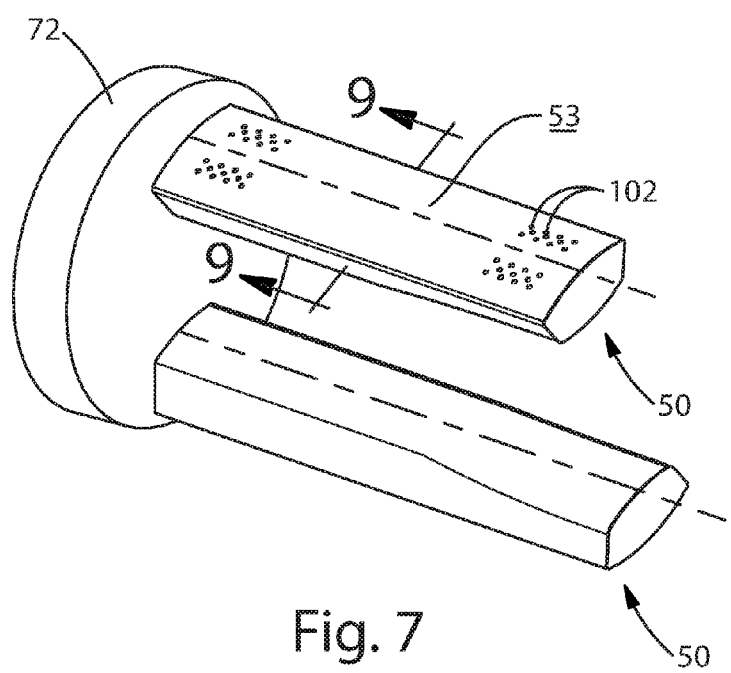
FIG. 7 is a perspective view of an example carrier member in accordance with the present disclosure.
Figure 8:
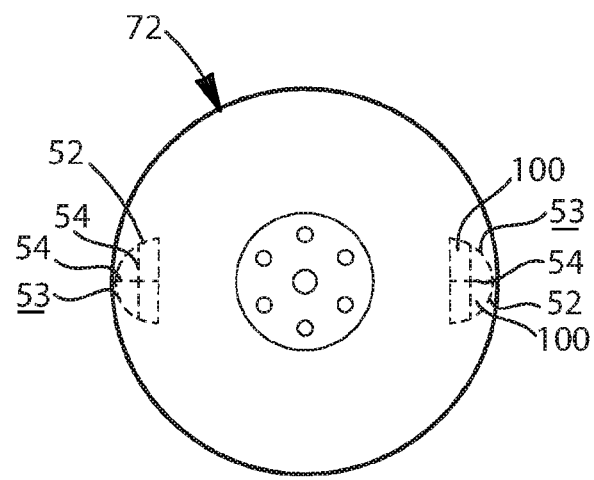
FIG. 8 is a rear view of the example carrier member of FIG. 7, in accordance with the present disclosure.
Figure 9:
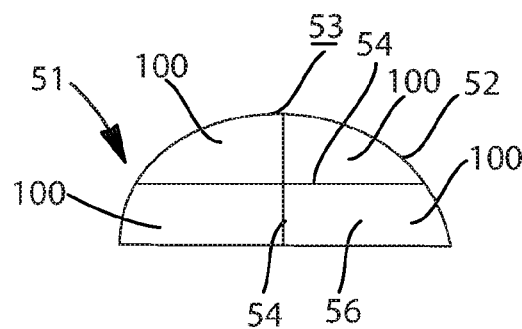
FIG. 9 is a cross-sectional view of a portion of the carrier member taken about line 9-9 of FIG. 7, in accordance with the present disclosure.

Referring to FIGS. 7-9, the carrier members 50 may each define one or more fluid channels or channels 100 therein. The outer surface 53 may define one or more fluid ports 102 therein. The one or more fluid ports 102 may be in fluid communication with the one or more channels 100 so that fluid pressure (positive and/or negative) may be applied to the articles 30 positioned on the outer surface 53 of the carrier members in locations where the articles 30 overlap the one or more fluid ports 102. The one or more channels 100 may be in fluid communication with one or more fluid pumps (see e.g., fluid pump 104 in FIG. 1) configured to provide a positive and/or negative fluid pressure to the channels 100. In a form, one fluid pump may be configured to provide a positive fluid pressure and another fluid pump may be configured to provide a negative fluid pressure to the channels 100. One or more of the fluid pumps may be in fluid communication with a manifold (not illustrated) which is in fluid communication with at least some of the channels 100. In such an instance, positive and/or negative fluid pressure may be provided by the manifold to the at least some channels 100 as desired and as will be recognized by those of skill in the art.

Referring to FIGS. 7 and 8, the carrier members of the present disclosure may comprise a housing 51 comprising a wall 52 and an outer surface 53, wherein at least a portion of the outer surface 53 may be configured to engage one or more articles to be transferred. The wall 52 may define an interior space 56 in the housing 51. A support member 54 may be at least partially positioned, or fully positioned within the interior space 56 of the housing 51. The support member 54 may be connected with (directly or indirectly) at least a portion of the wall 52. The support member 54 may be connected with the portion of the wall 52 using an adhesive or other joining technique. The support member 54, or portions thereof, may comprise one or more layers of carbon fiber, such as woven carbon fiber or uniaxial carbon fiber, as will be discussed in greater detail below. The housing 51 may comprise extruded aluminum or other suitable metal or material as discussed herein. Other portions of the carrier member 50 or the housing 51 may also comprise carbon fiber. In addition, the transfer members may comprise carbon fiber in one instance. By using a support member 54 comprising carbon fiber, such as one or more layers of a woven carbon fiber material or a uniaxial carbon fiber material, for example, the design of the overall geometry of the carrier member is not as limited compared to using an extruded aluminum housing formed with one or more extruded support members as one solid piece. Further, using a support member comprising carbon fiber allows for less aluminum to be used in the housing 51 owing to the strength of the carbon fiber material, thereby providing a lighter weight carrier member. This lighter weight can be very advantageous since the carrier member is orbited at a varying angular velocity.

Referring to FIG. 9, an example cross-sectional view of the carrier member 50 taken about line 9-9 of FIG. 7 is illustrated. The wall 52 forms the perimeter, or at least portion of the perimeter of the housing 51. A number of fluid channels 100 are formed within the housing 51 intermediate portions of the wall 52 (or outer surface 53) and portions of the support member 54. One or more fluid ports 102 (see FIG. 7) may be in fluid communication with one or more channels 100 so that a fluid pressure (positive and/or negative) may be provided to the fluid ports 102, as referenced above.

Each programmable motor may be in electrical communication with a motor control system for the programmable motor. The motor control system may comprise an amplifier or a controller, or both. Example motor control systems 70 are illustrated in FIGS. 1-6. The motor control system 70 may regulate, control, and/or vary the speed at which the programmable motor runs throughout an orbit, or partial orbit, of the carrier member 50 causing the carrier member 50 to increase or decrease in speed based on where it is in its rotational path (e.g., in the receiving zone 21, in the application zone 23, between the application zone 23 and a receiving zone 21, or between the receiving zone 21 and the application zone 23).

Figure 10:
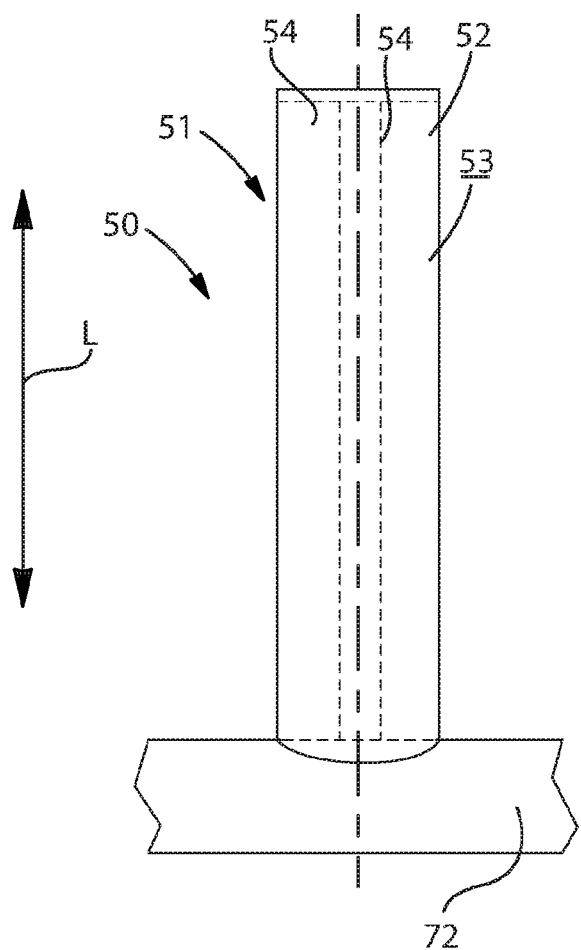
FIG. 10 is a top view of the carrier member of FIG. 7, in accordance with the present disclosure.
Figure 11:
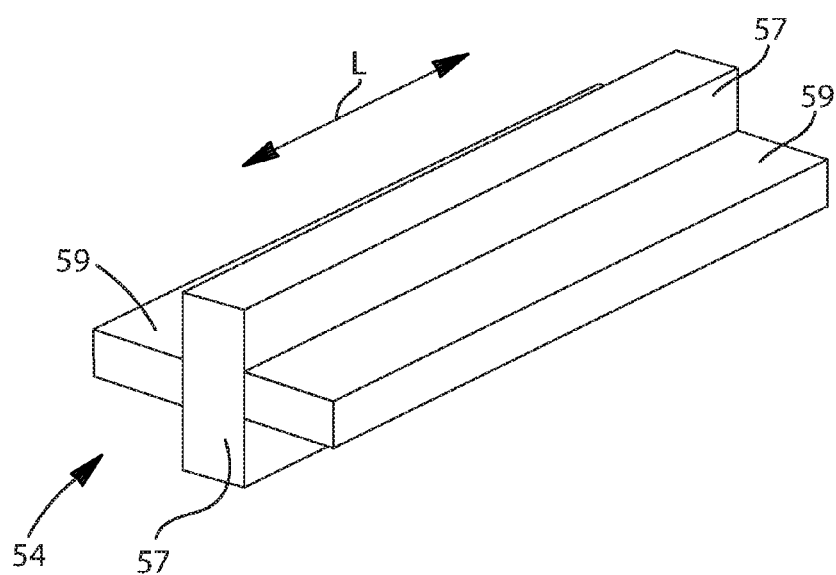
FIG. 11 illustrates a perspective view of an example carrier member of the present disclosure.

Referring to FIG. 10, a top view of the carrier member of FIG. 7 is illustrated. The carrier member 50 comprises a longitudinal axis, L. The support member 54 may comprise one or more layers of carbon fiber materials, such as woven carbon fiber materials, uniaxial, non-woven carbon fiber materials, or other non-woven carbon fiber materials. The carbon fiber provides a high-strength, low-weight material which is important for the orbiting carrier member 50. FIG. 11 illustrates a perspective view of an example support member 54 comprising one or more layers of carbon fiber. The longitudinal axis, L, in FIG. 11 correlates to the longitudinal axis, L, in FIG. 10. The support member 54 may comprise two fins 57 extending in directions opposite 15 to, or substantially opposite to, each other and another two fins 59 extending in directions opposite to, or substantially opposite to, each other. The fins 57 may extend in a direction transverse to or perpendicular to the direction of the fins 59. Also, in some situations, any suitable number of fins may be provided on a support member. The support member 54 may be formed as a single piece or may be formed of multiple pieces. The fins 57 may be formed of a single piece or multiple pieces and the fins 59 may be formed of a single piece or multiple pieces. In an instance, the support member may comprise a body, wherein the various fins may be connected to the body or formed with the body. In one instance, the support member 54 may comprise a material, such as aluminum or titanium, for example, and may have a sleeve at least partially, or fully, covering the material, wherein the sleeve comprises one or more layers of carbon fiber. This sleeve may provide additional strength to the support member 54 owing to the one or more layers of carbon fiber. The carbon fiber in the layers may be woven carbon fiber, uniaxial, non-woven carbon fiber, or other non-woven carbon fiber.

Figure 12:
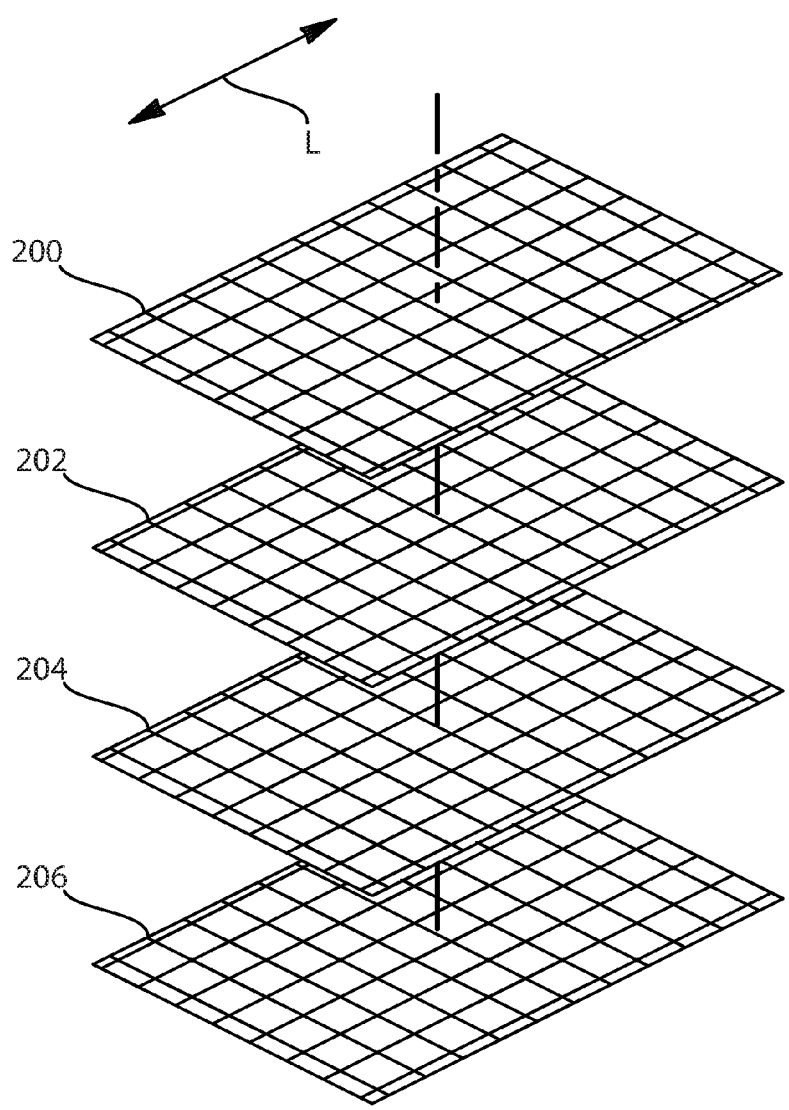
FIG. 12 illustrates example carbon fiber layering of a support member in accordance with the present disclosure.

A plurality of woven carbon fiber layers 200 of an example support member 54 or sleeve thereof are illustrated in FIG. 12. The woven carbon fibers layers 200, 202, 204, and 206 may form the fins 57 and 59 or outer portions thereof in a sleeve form. The woven carbon fiber layers 200, 202, 204, and 206 may each have a first carbon fiber material having a first carbon fiber orientation extending generally parallel to the longitudinal axis, L, (see FIG. 10) of the carrier member 50 and a second carbon fiber material having a second carbon fiber orientation extending generally perpendicular to the longitudinal axis, L. In other instances, the first and second carbon fiber orientations may be about 90 degrees from each other, but may not be parallel and perpendicular, respectively, to the longitudinal axis, L. In other forms, the first and second carbon fiber orientations may be any other suitable angle relative to each other and relative to the longitudinal axis, L. In other forms, the layers 200, 202, 204, and 206 may comprise uniaxial, non-woven carbon fiber or other non-woven carbon fiber, instead of woven carbon fiber. Although four carbon fiber layers 200, 202, 204, and 206 are illustrated in FIG. 12, as an example, any suitable number of carbon fiber layers may be used depending on the specific strength and/or performance attributes required for a particular support member or a portion thereof.

As expressed above, woven carbon fiber layers may not be used in the support member 54 (either as a sleeve or forming the support member 54) and, instead, carbon fiber layers having any suitable carbon fiber orientation relative to the longitudinal axis, L, may be used, such as uniaxial, non-woven carbon fiber materials, for example. Any suitable number of these layers may be used in certain instances.

In yet another instance, one or more woven carbon fiber layers and one or more non-woven carbon fiber layers may be used as a portion of (e.g., sleeve), or all of, the support member 54. In such an instance, any suitable number of woven or non-woven layers may be used as will be recognized by those of skill in the art.

In certain instances, regardless of whether woven or non-woven carbon fibers are used, a first portion (e.g., fins 57, or portions thereof) of the support member 54 may be formed using a first number of carbon fiber layers and a second portion (e.g., fins 59, or portions thereof) of the support member 54 may be formed using a second number of carbon fiber layers. The first and second numbers may be different.

Although the support member 54 is disclosed in a certain configuration as an example, many other suitable support member configurations are within the scope of the present disclosure as will be recognized to those of skill in the art. Furthermore, more than one support member may be present in a particular carrier member in some instances.

The thickness of a fin 57, 59 of the support member 54 may be dependent on how many carbon fiber layers are used in its formation and the thickness of each carbon fiber layer. In an instance, the fins may have thicknesses in the range of about 0.5 mm to about 3 mm, about 0.75 mm to about 2 mm, about 0.75 mm to about 1.5 mm, about 0.75 mm to about 1.25 mm, about 0.8 mm to about 1.2 mm, about 0.9 mm, about 0.95 mm, about 1 mm, or about 1.1 mm, specifically reciting all 0.01 mm increments within the above-specified ranges and all ranges formed therein or thereby. Other thicknesses of the fins of the support member 54 are also within the scope of the present disclosure based on specific design requirements for a certain application. Each carbon fiber layer of the fins may have a thickness in the range of about 0.1 mm to about 1 mm, about 0.1 mm to about 0.8 mm, about 0.2 mm to about 0.5 mm, about 0.2 mm to about 0.3 mm, or about 0.25 mm, specifically reciting all 0.01 mm increments within the above-specified ranges and all ranges formed therein or thereby. Other thicknesses of each carbon fiber layer of the fins of the support member are also within the scope of the present disclosure based on specific design requirements for certain applications.

Figure 13:
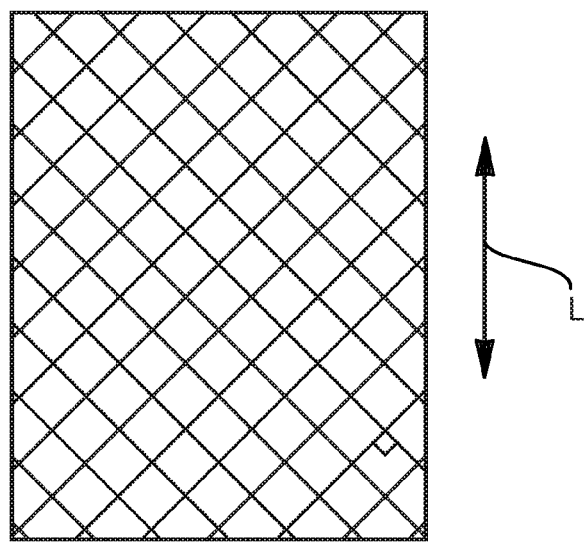
FIG. 13 illustrates an example woven carbon fiber pattern in accordance with the present disclosure.

An alternative woven carbon fiber material for the fins, or other portions of the support member 54 (e.g., sleeve) is illustrated in FIG. 13 as an example. In this instance, the woven carbon fiber material comprises a first carbon fiber material having a first carbon fiber orientation extending about 45 degrees from the longitudinal axis, L, of the carrier member 50 (see e.g., FIG. 10) and having a second carbon fiber material having a second carbon fiber orientation extending about 45 degrees from the longitudinal axis, L, of the carrier member 50. Other orientations relative of the first and second carbon fiber materials, relative to the longitudinal axis, L, are also within the scope of the present disclosure. It is to be noted that the fins, or other portions of the support member, may comprise any suitable combination of woven carbon fiber materials disclosed herein. A first woven carbon fiber layer may have a first woven pattern and a second woven carbon fiber layer may have a second woven pattern.

As referenced above, carbon fiber materials having uniaxial carbon fiber orientations or other non-woven orientation may be used in one layer, more than one layer, or all layers of a carbon fiber material. The uniaxial carbon fiber orientation may extend in a direction parallel, or substantially parallel, to the longitudinal axis, L, of the carrier members 50. In other instances, the uniaxial carbon fiber orientation may extend in a direction perpendicular to, substantially perpendicular to, or transverse to the longitudinal axis, L, of the carrier members. If more than one carbon fiber material is provided, a first carbon fiber layer may have a first uniaxial carbon fiber orientation extending in a first direction and a second carbon fiber layer may have a second uniaxial carbon fiber orientation extending in a second direction. The second direction may be the same as or different than the first direction.

A resin, adhesive, or other suitable material may be used intermediate the various layers to hold the carbon fiber layers of the support member 54 together. Other known carbon fiber layer joining techniques may also be used.

Each motor control system and programmable motor pair defines one or more excitation frequencies. The carrier member, including the support member comprising carbon fiber, defines one or more natural frequencies. Each natural frequency may be at least about 1.1 times greater than or at least about 1.1 times less than each excitation frequency. Each natural frequency may also be at least about 1.05 to about 5 or about 2 times greater than or at least about 1.05 to about 5 or about 2 times less than each excitation frequency, specifically reciting all 0.01 increments within the specified ranges and all ranges formed therein or thereby. This helps eliminate coincidence with the one or more natural frequencies and the one or more excitation frequencies.

By eliminating coincidence with the one or more natural frequencies of the carrier member comprising the support member comprising carbon fiber and the one or more excitation frequencies of the motor control system and the motor, carbon fiber may now be used in the construction of carrier members comprising support members comprising carbon fiber without cracking, or without substantial cracking of the carbon fiber, thereby allowing for carrier members that have high strength, light weight, and provide a greater range of design options for the carrier member.

In a form, the present disclosure may use a component, formed at least partially of carbon fiber, in any portion of an absorbent article manufacturing or processing line or manufacturing or processing line for any other product or intermediate product (hereafter absorbent article processing line). In a form, the present disclosure may use a component, formed at least partially of carbon fiber, in a portion of a piece of equipment of an absorbent article processing line. In a form, the present disclosure may use a component, formed at least partially of carbon fiber, in a transfer apparatus of an absorbent article processing line. In a form, the present disclosure may use a component, formed at least partially of carbon fiber, in a transfer head of a transfer apparatus of an absorbent article processing line. The various components, formed at least partially of carbon fiber, discussed above may be manufactured such that their natural frequency is shifted at least 1.1 times greater than or at least 1.1 times less than (or other ranges specified herein) various excitation frequencies emitted by equipment and/or control systems of an absorbent article processing line. The various components, formed at least partially of carbon fiber, are desirable in view of them being high strength, low weight, and durable materials that may be used during high speed movements (e.g., accelerations, decelerations) for achieving high throughput in absorbent article processing lines.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An apparatus for transferring one or more articles from a first carrier moving at a first speed to a second carrier moving at a second speed that is different than the first speed, the apparatus comprising:
   a programmable motor,
   a carrier member operably engaged with the programmable motor, the carrier member comprising:
      a housing comprising a wall defining an interior space and an outer surface configured to receive the one or more articles from the first carrier in a receiving zone and configured to deposit the one or more articles onto the second carrier in an application zone; and
      a support member comprising carbon fiber at least partially positioned within the interior space of the housing and connected with a portion of the wall;
   wherein the programmable motor is configured to move the outer surface of the carrier member at a third speed through the receiving zone and at a fourth speed through the application zone; and
   a motor control system for the programmable motor, wherein the motor control system and the programmable motor define an excitation frequency, wherein the carrier member defines a natural frequency, and wherein the natural frequency is at least 1.1 times greater than or at least 1.1 times less than the excitation frequency.

2. The apparatus of claim 1, wherein the natural frequency is at least 1.2 times greater than or at least 1.2 times less than the excitation frequency.

3. The apparatus of claim 1, wherein the housing comprises aluminum.

4. The apparatus of claim 1, comprising a channel defined between a portion of the support member and the outer surface.

5. The apparatus of claim 4, comprising a fluid port in the outer surface that is in fluid communication with the channel, wherein the fluid port is configured to provide a fluid pressure to an article being transferred.

6. The apparatus of claim 1, comprising a transfer member engaged with the carrier member and the programmable motor.

7. The apparatus of claim 6, wherein the programmable motor rotates the transfer member about an axis of rotation.

8. The apparatus of claim 7, wherein the transfer member rotates the carrier member about the axis of rotation.

9. The apparatus of claim 1, wherein the third speed is substantially equal to the first speed, and wherein the fourth speed is substantially equal to the second speed.

10. The apparatus of claim 1, wherein the programmable motor comprises a programmable rotary motor.

11. The apparatus of claim 1, wherein the programmable motor comprises a programmable linear motor.

12. An apparatus for transferring one or more articles from a first carrier to a second carrier, the apparatus comprising:
a first programmable motor;
a second programmable motor;
a first carrier member operably engaged with the first programmable motor, wherein the first programmable motor is configured to rotate the first carrier member in an orbital path, the first carrier member comprising:
a housing comprising a wall defining an interior space and an outer surface configured to receive the one or more articles from the first carrier in a receiving zone and configured to deposit the one or more articles onto the second carrier in an application zone; and
a support member comprising carbon fiber at least partially positioned within the interior space of the housing and attached to a portion of the wall;
a second carrier member operably engaged with the second programmable motor, wherein the second programmable motor is configured to rotate the second carrier member in the orbital path, the second carrier member comprising:
a housing comprising a wall defining an interior space and an outer surface configured to receive the one or more articles from the first carrier in the receiving zone and configured to deposit the one or more articles onto the second carrier in the application zone; and
a support member comprising carbon fiber at least partially positioned within the interior space of the housing and attached to a portion of the wall;
wherein the first and second carrier members are located at least partially between the first and second programmable motors; and
a motor control system for the first programmable motor, wherein the motor control system and the first programmable motor define an excitation frequency, wherein the first carrier member defines a natural frequency, and wherein the natural frequency is at least 1.1 times greater than or at least 1.1 times less than the excitation frequency.

13. The apparatus of claim 12, wherein the first carrier member defines a natural frequency, and wherein the natural frequency is at least 1.2 times greater than or at least 1.2 times less than the excitation frequency.

14. The apparatus of claim 12, wherein the first programmable motor or the second programmable motor comprises a programmable rotary motor.

15. The apparatus of claim 12, wherein the first programmable motor or the second programmable motor comprises a programmable linear motor.

16. The apparatus of claim 12, comprising:
a channel defined between a portion of the support member and the outer surface of the first carrier member;
a fluid source in fluid communication with the channel; and
a fluid port in the outer surface of the first carrier member and in fluid communication with the channel.

17. An apparatus for transferring one or more articles from a first carrier to a second carrier, the apparatus comprising:
a first programmable motor;
a second programmable motor;
a first transfer member operably engaged with the first programmable motor;
a second transfer member operably engaged with the second programmable motor, wherein the first and second transfer members are generally aligned with respect to a common axis;
a first carrier member connected with the first transfer member, wherein the first transfer member is configured to guide the first carrier member in an orbital path, the first carrier member comprising:
a housing comprising a wall defining an interior space and an outer surface configured to receive the one or more articles from the first carrier in a receiving zone and configured to deposit the one or more articles onto the second carrier in an application zone; and
a support member comprising carbon fiber positioned at least partially within the interior space of the housing and connected with a portion of the wall;
a second carrier member connected with the second transfer member, wherein the second transfer member is configured to guide the second carrier member in the orbital path, the second carrier member comprising:
a housing comprising a-wall defining an interior space and an outer surface configured to receive the one or more articles from the first carrier in the receiving zone and configured to deposit the one or more articles onto the second carrier in the application zone; and
a support member comprising carbon fiber at least partially positioned within the interior space of the housing and connected with a portion of the wall; and
a motor control system for the first programmable motor, wherein the motor control system and the first programmable motor define an excitation frequency, wherein each carrier member defines a natural frequency, and wherein the natural frequency is at least 1.1 times greater than or at least 1.1 times less than the excitation frequency.

18. The apparatus of claim 17, wherein the natural frequency is at least 1.2 times greater than or at least 1.2 times less than the excitation frequency.

19. The apparatus of claim 17, wherein the first programmable motor comprises a programmable rotary motor.

20. The apparatus of claim 17, wherein the first programmable motor comprises a programmable linear motor.

21. The apparatus of claim 17, comprising a stationary shaft rotatably supporting the first and second transfer members, wherein the stationary shaft is coaxially oriented along the common axis.

22. The apparatus of claim 17, wherein the carbon fiber of the support member of the first carrier member comprises a plurality of layers of woven carbon fiber material.

* * * * *